(12) United States Patent
Hamilton

(10) Patent No.: US 10,441,511 B2
(45) Date of Patent: Oct. 15, 2019

(54) SYSTEMS, DEVICES, AND/OR METHODS FOR MANAGING MEDICAMENT DISPENSER

(71) Applicant: Joseph Hamilton, Afton, VA (US)

(72) Inventor: Joseph Hamilton, Afton, VA (US)

(*) Notice: Subject to any disclaimer, the term of this patent is extended or adjusted under 35 U.S.C. 154(b) by 0 days.

(21) Appl. No.: 16/028,480

(22) Filed: Jul. 6, 2018

(65) Prior Publication Data

US 2019/0070075 A1 Mar. 7, 2019

Related U.S. Application Data

(60) Provisional application No. 62/604,481, filed on Jul. 10, 2017.

(51) Int. Cl.
| | |
|---|---|
| *A61J 7/04* | (2006.01) |
| *A61J 7/00* | (2006.01) |
| *G16H 20/13* | (2018.01) |
| *A61J 1/03* | (2006.01) |

(52) U.S. Cl.
CPC ............ *A61J 7/0445* (2015.05); *A61J 7/0076* (2013.01); *A61J 7/0418* (2015.05); *A61J 7/0481* (2013.01); *G16H 20/13* (2018.01); *A61J 1/035* (2013.01)

(58) Field of Classification Search
CPC .... A61J 1/035; A61J 7/0076; A61M 15/0026; A61M 15/0043; A61M 15/0045
See application file for complete search history.

(56) References Cited

U.S. PATENT DOCUMENTS

| | | | | |
|---|---|---|---|---|
| 3,651,927 A * | 3/1972 | Richardson | ........ | B65D 83/0463 221/5 |
| 3,904,075 A * | 9/1975 | Richardson | ............... | A61J 7/04 221/5 |
| 4,015,717 A * | 4/1977 | Richardson | ............... | A61J 7/04 206/534 |
| 4,915,256 A * | 4/1990 | Tump | ................. | B65D 83/0463 116/308 |
| 4,971,221 A * | 11/1990 | Urquhart | ............ | B65D 83/0454 221/2 |
| 5,988,429 A * | 11/1999 | Coe | ..................... | B65D 83/0463 206/531 |
| 6,062,420 A * | 5/2000 | Krouwel | ............ | B65D 83/0463 221/5 |
| 7,950,389 B2 * | 5/2011 | Eason | ............... | A61M 15/0028 128/203.12 |
| 7,987,845 B2 * | 8/2011 | King | ................. | A61M 15/0028 128/203.12 |
| 8,161,968 B2 * | 4/2012 | Augustyn | ......... | A61M 15/0045 128/203.15 |
| 8,381,720 B2 * | 2/2013 | Thoemmes | ....... | A61M 15/0045 128/203.21 |
| 8,434,476 B2 * | 5/2013 | Von Schuckmann | ....................... | A61M 15/0045 128/200.24 |

(Continued)

*Primary Examiner* — Jacob S. Scott
*Assistant Examiner* — Ayodeji T Ojofeitimi
(74) *Attorney, Agent, or Firm* — Dale Jensen, PLC; Dale Jensen

(57) ABSTRACT

Certain exemplary embodiments can provide a system that comprises a case. The case comprises a body comprising a lever. The body defines a cover latch aperture and a dispensing port. The case comprises a cover coupled to the body via a hinge. The cover is releasably closeable with the body via a cover latch and the cover latch aperture.

11 Claims, 11 Drawing Sheets

(56) References Cited

U.S. PATENT DOCUMENTS

| | | | | |
|---|---|---|---|---|
| 8,474,453 B2* | 7/2013 | Eason | ............... | A61M 15/0045 128/203.15 |
| 8,746,242 B2* | 6/2014 | Connell | ............ | A61M 15/0045 128/203.21 |
| 8,931,479 B2* | 1/2015 | Keegstra | ........... | A61M 15/0045 128/203.12 |
| 8,931,480 B2* | 1/2015 | Meliniotis | ......... | A61M 15/0045 128/203.21 |
| 2002/0030062 A1* | 3/2002 | Garrant | ............. | B65D 83/0409 221/87 |
| 2005/0177275 A1* | 8/2005 | Harvey | ............ | A61M 15/0083 700/244 |
| 2006/0283876 A1* | 12/2006 | Mocnik | ................ | A61J 7/0409 221/300 |
| 2010/0059052 A1* | 3/2010 | Davies | .................... | A61J 1/035 128/203.15 |
| 2011/0101016 A1* | 5/2011 | Luciano, Jr. | .......... | A61J 7/0084 221/1 |
| 2011/0108567 A1* | 5/2011 | Giraud | ............... | B65D 83/0409 221/261 |
| 2011/0253737 A1* | 10/2011 | Portney | .............. | B65D 83/0454 221/277 |
| 2012/0160863 A1* | 6/2012 | Thompson | ......... | B65D 83/0409 221/8 |
| 2013/0168405 A1* | 7/2013 | Yuyama | .................. | G07F 11/42 221/151 |
| 2017/0197748 A1* | 7/2017 | Fagen | ..................... | A61J 1/035 |
| 2017/0197775 A1* | 7/2017 | Fagen | ................. | B65B 69/0033 |

* cited by examiner

6000

6100

7000

7100

SYSTEMS, DEVICES, AND/OR METHODS FOR MANAGING MEDICAMENT DISPENSER

CROSS-REFERENCES TO RELATED APPLICATIONS

This application claims priority to, and incorporates by reference herein in its entirety, U.S. Provisional Patent Application Ser. No. 62/604,481, filed Jul. 10, 2017.

BRIEF DESCRIPTION OF THE DRAWINGS

A wide variety of potential practical and useful embodiments will be more readily understood through the following detailed description of certain exemplary embodiments, with reference to the accompanying exemplary drawings in which.

DETAILED DESCRIPTION

Figure 1:
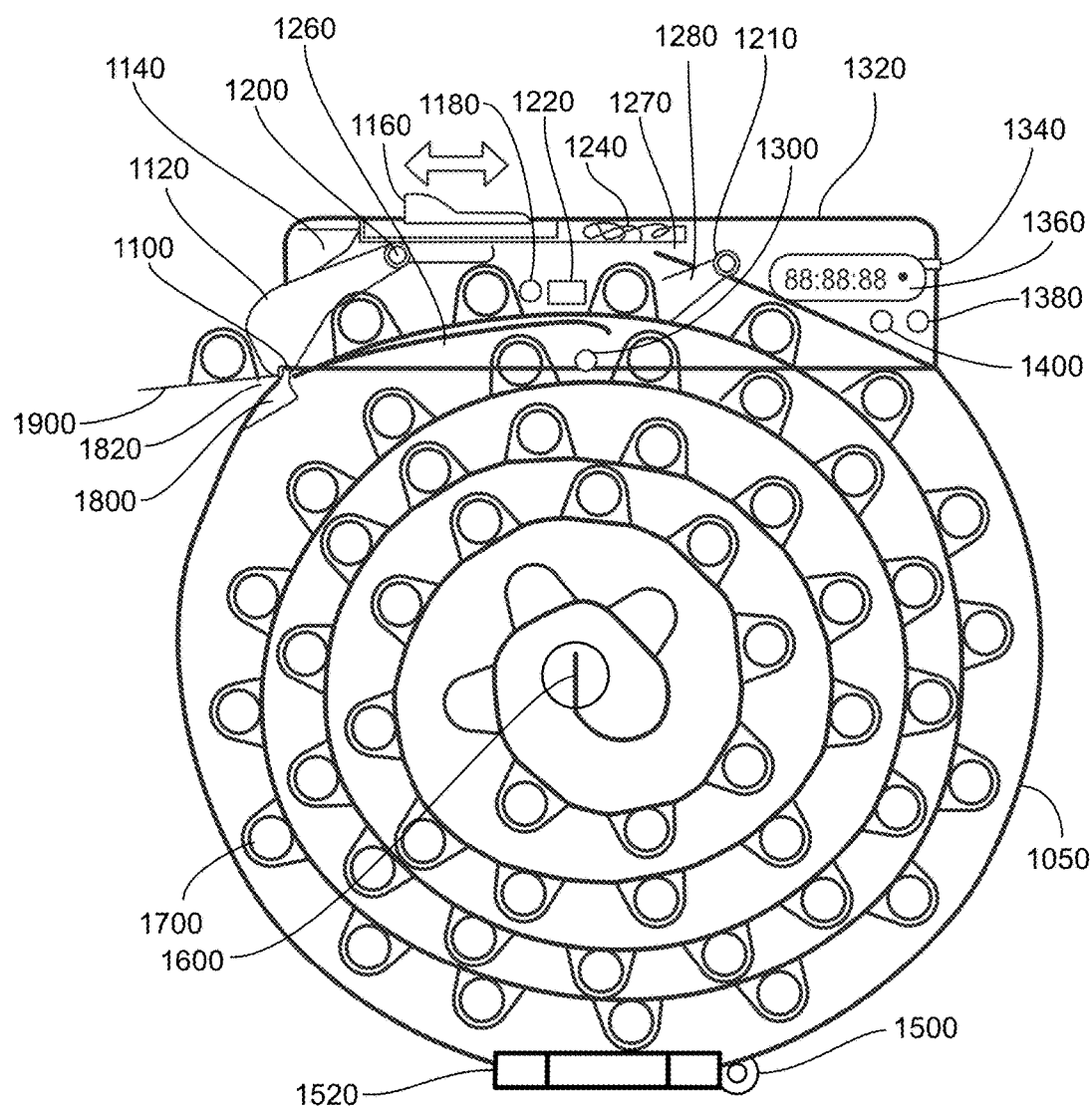
FIG. 1 is a cutaway view of a diagram of an exemplary embodiment of a dose compliance recording tablet blister dispenser 1000.

Certain exemplary embodiments can provide a system that comprises a case. The case comprises a body comprising a lever. The body defines a cover latch aperture and a dispensing port. The case comprises a cover coupled to the body via a hinge. The cover is releasably closeable with the body via a cover latch and the cover latch aperture.

Certain exemplary embodiments provide a device that dispenses one dose of medicine or other small object (e.g. prescription tablet, natural product compression like marijuana, capsule, and/or powder, etc.) at a time. Certain exemplary devices can record the date/time that the medicine, which is comprised in a segmented strip of blisters, is dispensed and store that actual date/time in onboard memory, which can later be viewed along with the time each dose in the strip was taken on its display or downloaded via wireless or hardwire communication to an external computer system (e.g. a pharmacy information device, an information device of a medical professional, and information device of a user, a cell phone, and/or other information devices). The device can comprise a locking mechanism which is internal to the device that can use the prescription schedule information downloaded to a memory of the device. For example, a pharmacist when filling the prescription can activate the locking mechanism. As another example, the device can be preprogrammed by a manufacturer to physically prevent the device from being operated to dispense the dose until an allotted time or elapsed time between doses or until proper identification (e.g. fingerprint identification is detected by optional finger print sensor, entry of button sequence or partial finger print sensor) is provided by the user. By recording the time (timestamp) at which each blister section is dispensed and/or using a locking mechanism to stop medicine from being dispensed before schedule time. Via the locking mechanism, the device either stops medicine from being dispensed until scheduled time or makes it apparent upon error recorded and optionally displayed on device. In certain exemplary embodiments, the device will case functioning until returned to a medical professional or a pharmacy if the medicine is dispensed out of schedule compliance. Such embodiments can be a significant deterrent for diversion of dangerous prescription drugs to elicit markets. A dispense sensor and/or additional sensor used for detection of blister strip advancement may be positioned and programmed to detect tampering patterns (e.g. by abnormal sequence or timing of sensor activation) such that exemplary embodiments cannot be tampered by external means without detection.

The blister strip can be a foil back moisture proof, child proof, plastic blister packs used for many medicines. Certain exemplary embodiments utilize a long linear single line of blister segments, each comprising a dose of medicine or other object (e.g. a tablet). Each segment of the blister strip is perforated for easy detachment by the user, and each segment has a portion of the strip removed on one or both sides of the strip to further make detachment of segment easier and also mates up with protrusions at the exit of the device such that the blister strip from behind the segment already in position for user detachment is held in place while the user detaches the blister segment external to the device; this prevents the blister strip from being inadvertently advanced during blister section detachment. The dispense latch assembly can define holes that mate with the above mentioned protrusions to further hold the strip in place while the dispense blister segment is manually torn off. The dispense latch assembly is further held down when in the dispensed position by a bent spring. In one option of blister strip the blister may be closed with a snap in segment or strip of segments. The snap in backing is made of similar flexible material as the blister and is matted with a recessed channel around the parameter of upper lip of the blister to form an air tight seal when depressed in place. Another form of seal can be produced by having either the blister half of the strip or the snap in half of the strip having a malleable sealing material, which is located such that the when the snap in segment is pressed into the blister half of the strip, that the matted surfaces compress against the malleable material creating an airtight seal. An edge of the snap in segment can be constructed such that a portion along the long way edge of the strip is bent away from the blister half of the strip therefore making is easier to grasp to remove the snap in segment to get the medication out of the blister. Another option is to mold the matted sealed portion above the flat portion of the blister half of the strip and have the snap in half of the strip snap around the portion of the blister half of the strip.

An alternative to conventional blister packing design described above utilizes a tube of thin plastic like film where the object to be dispensed is located and isolated within segments (similar to what is used to package candy in a string of individual and isolated segments) of thin film shaped into a tube shape (e.g. by heat-sealing between segments which may be perforated to facilitate detachment upon dispensing). Various processes for locating objects to be dispensed within a long chain or segments of a tube shape holder or for blister packing are well known to those skilled in the art and are therefore not covered in any detail herein. The blister pack described herein, as well as the segmented thin film tube described above, can be layered in snake like fashion with alternating holders from the coil design described more fully herein. For example the linkages of blisters or thin film tube segments can be loaded in a layering fashion inside of a holder having dimensions to accommodate a desired number of tablets held by each; such a holder can have an appearance of a prescription medicine bottle or an enlarged tic tac (tic tac is a registered trademark of Ferrero S.P.A. Corporation of Italy) box for example with working mechanism constructed to dispense segments located atop the holder.

The blister strip or alternate can be loaded in various ways, such as via a preformed coil inserted into the device via the hinged cover access or reeled in through the exit hole. Such embodiments can utilize a keyed load tool similar to a crank to wind in the strip after the end of the strip is fed through the exit tool and through a partial slot in the center guide pin or similar holding mechanism. The center guide pin is free spinning and does not hold the end of the strip as the blisters are dispensed.

After the blister strip is loaded into the device and the cover is closed, the prescription label is affixed over a cover latch to act as a tamper proof seal. Device also comprises a sensor (e.g. contact, magnetic, light based etc), which can detect if the device is opened. This sensor is interfaced with an internal information device that is constructed to record if the cover is tampered with. A memory of the information device can comprise prescription and user information, which can be downloaded by the pharmacist's computer system (e.g. prescription number, drug information, user drivers license number, pharmacy and pharmacist id information, user information, insurance information etc). Parts of all of the information can be stored in the information device's memory as encrypted data which only can be accessed and read by appropriate computer systems (e.g. pharmacy computer systems with decoding software).

In certain exemplary embodiments, the device comprises a microprocessor, battery, memory, software, radio frequency circuitry, voice simulator, optional communication port and sensors (e.g. light, magnetic, contact) optional GPS locator and hard wire and wireless communication port. These components are used with an internal microprocessor clock with date and time values. One sensor is positioned to detect when the blister strip is advance to dispense a segment. The software monitors the sensor input and save the date/time value for each segment dispensed and store those values in memory for later retrieval by wire or wireless download. All electronic components can be comprised within water proof sub-assemblies or within sealed compartments of the device.

The device electronics comprise an LED, a sound element (beeper), and/or a vibration element that are communicatively coupled to the information device and can be used to notify the user when a dose is due. The device user interface (e.g. an LCD) and input buttons can be used to display time till next dose and/or recall dose history stored in the device's memory (e.g. tablet number, date, and/or time, etc.). The user interface can also display number of doses left or dispensed.

The device can comprise an optional fingerprint sensor communicatively coupled to the electronics. The finger print sensor is used to determine if the correct user is attempting to dispense medicine from the device. In certain exemplary embodiments, the device program logic only unlocks the advance of blister in the device when the correct user fingerprint is scanned and recognized. In certain exemplary embodiments, the device can be programmed without locking feature to record in device memory the positive or negative confirmation of correct fingerprint for each dose dispensed. To program the target user fingerprint, initially a scan of the intended user fingerprint can be made by a fingerprint sensor interfaced to an information device of a medical provider and/or a pharmacy and/or the device fingerprint sensor itself. The intended user's fingerprint data can be stored in the device memory to be used each time prior to a dose being dispensed by the device. One form of fingerprint sensor used maybe only be a small partial finger print sensor (e.g., approximately ½ inch) as such embodiments do not need to capture the full fingerprint for the targeted patent and/or caregiver. The full fingerprint can be captured at the pharmacy and information needed downloaded to the device memory and used to determine if a portion of the full finger print is confirmed by the patient or caregiver prior to unlocking the device and/or recording appropriate dispense event. A sequence of finger print identifications can be used as a code for access. Each fingerprint identification can be noted by a user interface or other indication (e.g. vibration, display) to let the user know when to progress the next finger print identification.

Device may be fitted with one or more buttons or other hand manipulated devices located in appropriate positions (e.g. either one or both sides of the device) and constructed to be depressed and/or manipulated to enable the main blister advance lever to dispense a blister segment. These buttons or equivalent are positioned and constructed as to lock in the relaxed position either through mechanical interference with the movement of the main blister lever or to communicate an electrical signal to the controller such that appropriate logic can engage the locking mechanism described in earlier paragraph to prevent the dispensing operation. In the depressed or actuated position the button(s) or equivalent are constructed to send a signal to the controller to temporarily electronically disengage the lock or mechanically remove the mechanical interference from the main blister lever and allow dispensing of a blister segment. These buttons or equivalent (e.g. slide(s) can be positioned in such a way as to prevent children from dispensing blister segments (e.g. in a position or multiple positions that only adults fingers could reach or adult strength could depress or actuate).

FIG. 1 is a cutaway view of a diagram of an exemplary embodiment of a dose compliance recording tablet blister dispenser 1000, which comprises:

A case 1050;
A dispense latch lock 1100;
A dispense latch 1120;
A bent spring 1140;
A linear thumb slide 1160 to dispense blister;
A sensor 1180 (e.g., a side looking optical sensor);
A first spring loaded lever 1200 and a second lever 1210 that are constructed to provide downward spring pressure on latches and/or to allow advancement of a blister strip comprised by dose compliance recording tablet blister dispenser 1000;
A lock 1220;
A spring 1240;

A first guide 1260 and a second guide 1270;

A reverse latch 1280

A tamper detection sensor 1300;

A biometric (e.g., fingerprint) sensor 1320;

A hardwire communication port 1340;

An electronics assembly 1360 (e.g., an information device, central processing unit, battery, memory device, radio frequency communication circuitry, digital display, light emitting diode display, and/or beeper, etc.); in certain exemplary embodiments, electronics assembly 1360 can be encapsulated and/or substantially waterproof;

A sound transducer (e.g., beeper) 1380;

A light emitting diode 1400;

An aperture constructed to receive a wrist strap 1500;

A hinge 1520;

A split center pin 1600;

A childproof and/or moisture proof blister 1700, which comprises a tablet;

A two prong blister segment holder 1800, which is constructed to allow for easy tear off without advancing the blister strip further;

A dispensing port 1820; and/or

A coiled blister strip 1900 (e.g., which comprises tablets).

Figure 2:
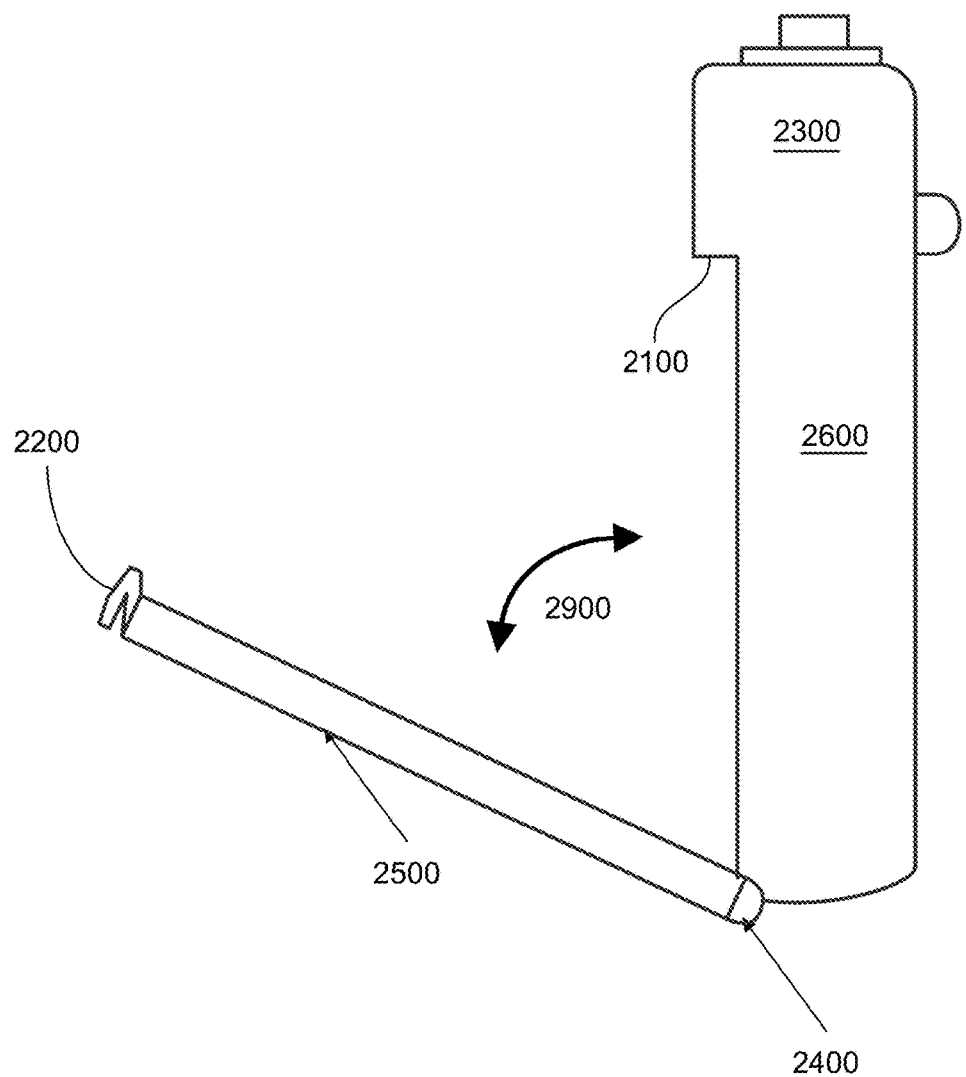
FIG. 2 is a block diagram of an exemplary embodiment of a system 2000.

Certain exemplary embodiments provide a case 1050 comprising:

a body (see, e.g., body 2600 as shown in FIG. 2) comprising a first lever 1200 and a second lever 1210, the body defining a cover latch aperture (see, e.g., cover latch aperture 2100 as shown in FIG. 2) and dispensing port 1820;

a cover (see, e.g., cover 2500 as shown in FIG. 2) coupled to the body via hinge 1520, wherein the cover is releasably closeable with the body via a cover latch (see, e.g., cover latch 2200 as shown in FIG. 2) and the cover latch aperture (see, e.g., cover latch aperture 2100 as shown in FIG. 2);

split center pin 1600, which can be keyed, that is constructed to engage with a first end of blister strip 1900;

a first guide 1260 and a second guide 1270 that align blister strip 1900 with dispensing port 1820, wherein first guide 1260 is at least in partial contact with blister strip backing; and a first dispense latch 1120 constructed to lift as a tablet comprised by blister strip 1900 passes to dispensing port 1820;

a dispense latch lock 1100 that engages with first dispense latch 1120; and allows a tearing of the blister strip 1900 substantially without advancing blister strip 1900 in case 1050; and Case 1050 can be constructed to release a tablet from blister strip 1900 responsive to movement of the lever. Case 1050 can be substantially waterproof. Lever 1200 can be a linear thumb slide. An information device (comprised by electronics assembly 1360) coupled to case 1050. The information device can be constructed to control dispensing of tablets from the blister strip responsive to a biometric identification of a user (e.g., via biometric sensor 1320). A fingerprint sensor (which can be biometric sensor 1320) can be constructed to transmit a signal indicative of a fingerprint of an authorized user such that a tablet is dispensed from case 1050. Tamper detection sensor 1300 can be constructed to indicate when the cover is opened.

A load tool (see load tool 9000 of FIG. 9) is constructed to engage with the split center pin 1600, wherein a user loads blister strip 1900 in case 1050 via rotation of the load tool.

Figure 3:
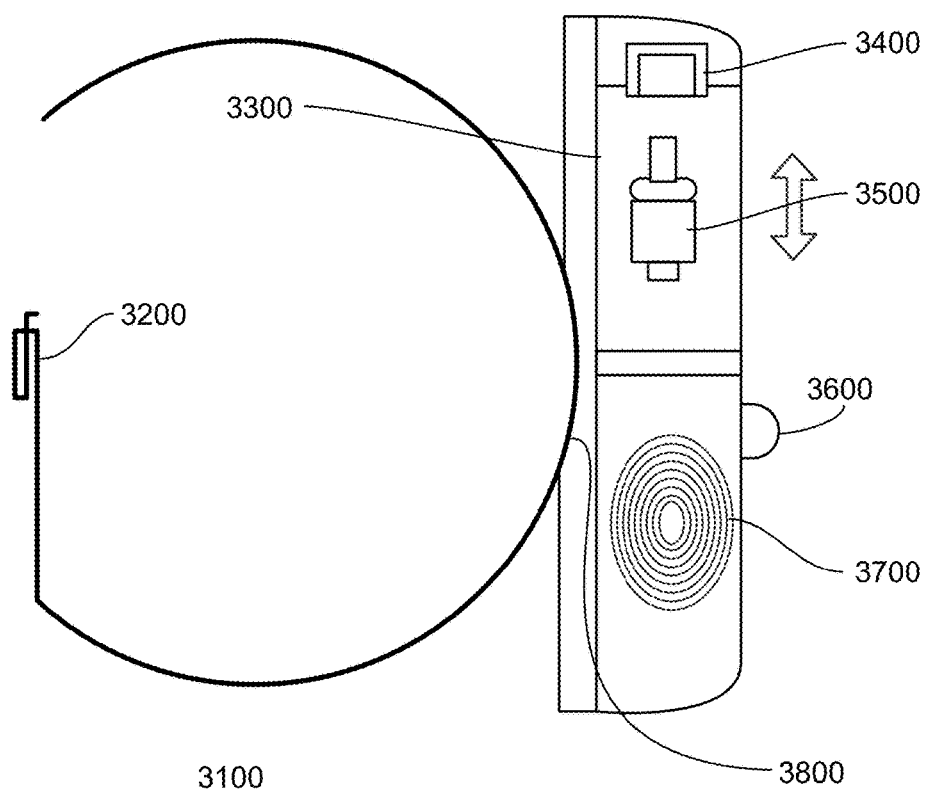
FIG. 3 is a block diagram of an exemplary embodiment of a system 3000.

A childproof button (see e.g., childproof button 3600 as shown in FIG. 3) constructed to, when in a locked position, resist dispensing of a tablet.

Certain exemplary systems can comprise sound transducer 1380 that generates an audible sound in response to an action of a user related to dispensing a tablet from blister strip 1900. A light (e.g., light emitting diode 1400) can generate a visible illumination in response to an action of a user related to dispensing a tablet from blister strip 1900. Second guide that 1270 resist motion of the blister strip away from the first guide as a tablet of the blister strip approaches the dispensing port.

FIG. 2 is a block diagram of an exemplary embodiment of a system 2000, which comprises a cover latch 2200, a hinge 2400, a cover 2500, a body 2600, and a case 2300. Case 2300 defines a cover latch aperture 2100, which is constructed to hold cover 2500 closed when engaged with aperture 2100. Cover 2500 swings in an arc 2900 when being opened and/or closed.

FIG. 3 is a block diagram of a plan view of an exemplary embodiment of a system 3000, which comprises:

A case 3100;

A cover latch 3200, which, once closed, has a tamper label affixed to provide an indication of tampering if the label is disturbed;

A tamper detection sensor 3300;

An exit 3400;

A linear blister tablet dispense lever 3500, which moves linearly back and forth (as indicated by the two-way arrow);

A childproof button 3600, which is constructed to electronically and/or mechanically disengage a lock when activated;

A biometric (e.g., fingerprint) sensor 3700; and

A case hinge 3800.

Figure 4:
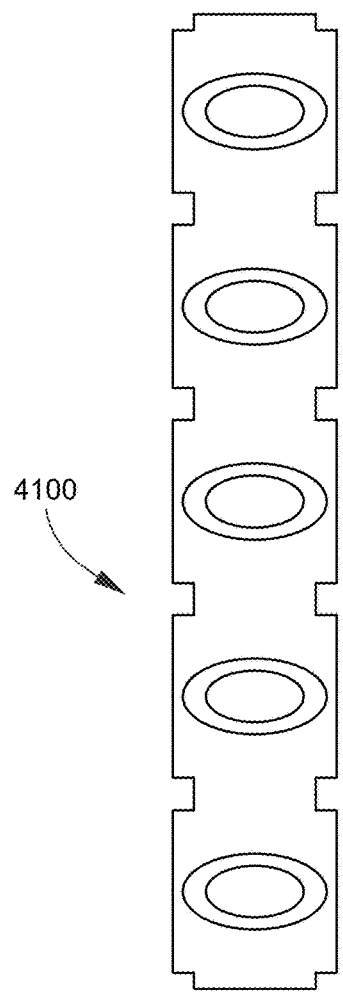
FIG. 4 is a block diagram of an exemplary embodiment of a blister strip 4000.

FIG. 4 is a block diagram of an exemplary embodiment of a blister strip 4000, which comprise a punch through type blister backing. Blister strip 4000 defines indentations 4100 with perforated seams between blisters for easy tear off.

Figure 5:
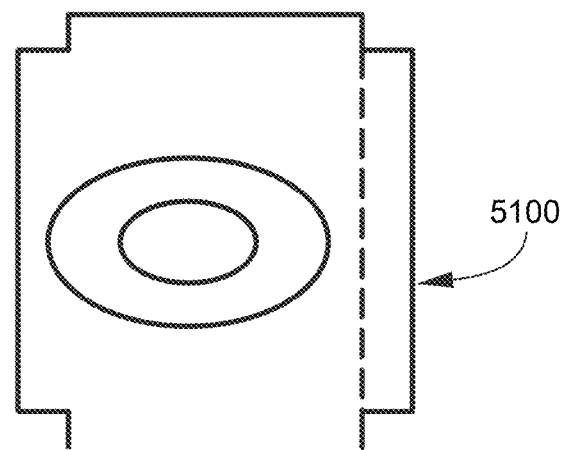
FIG. 5 is a block diagram of an exemplary embodiment of a portion of a blister strip 5000.

FIG. 5 is a block diagram of an exemplary embodiment of a portion of a blister strip 5000, which comprises a tear off backing 5100. Backing 5100 can be left unfixed along an edge for relatively easy removal.

Figure 6:
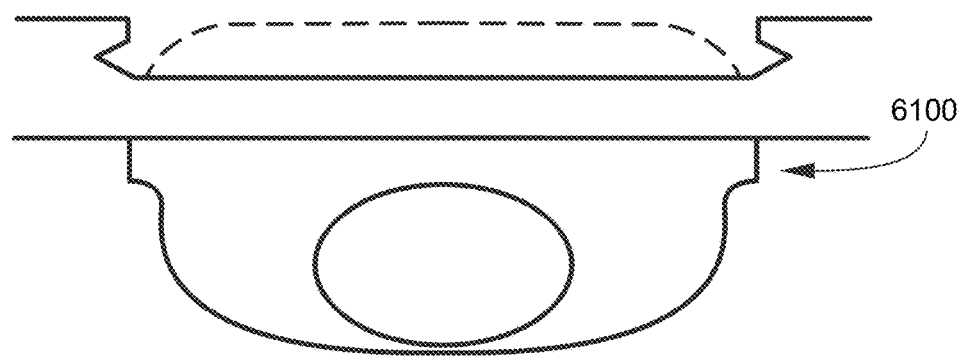
FIG. 6 is a block diagram of an exemplary embodiment of a portion of a blister strip 6000.

FIG. 6 is a block diagram of an exemplary embodiment of a portion of a blister strip 6000, which comprises a mated seal edge 6100. FIG. 6 is a side view of a modified (male) snap in blister backing (individual snap in segments or multiple segments in strip form). Blister strip seams snap in tight.

Figure 7:
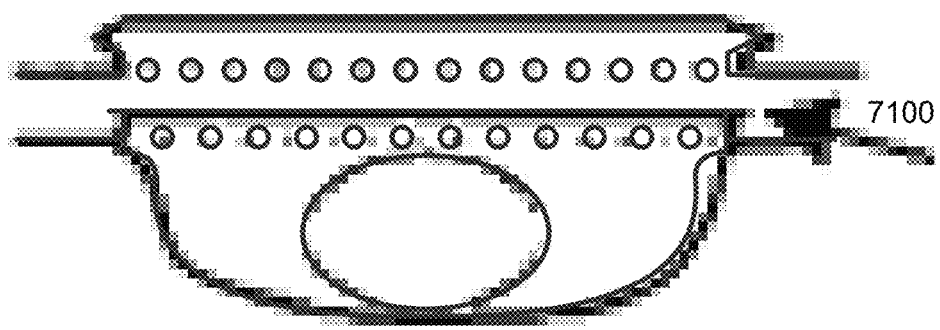
FIG. 7 is a block diagram of an exemplary embodiment of a portion of a blister strip 7000.

FIG. 7 is a block diagram of an exemplary embodiment of a portion of a blister strip 7000. FIG. 7 is a side view of a second modified (female) snap in blister backing (individual snap in segments or multiple segments in strip form). A mated seal edge 7100 of a blister strip segment snaps in tight.

Figure 8:
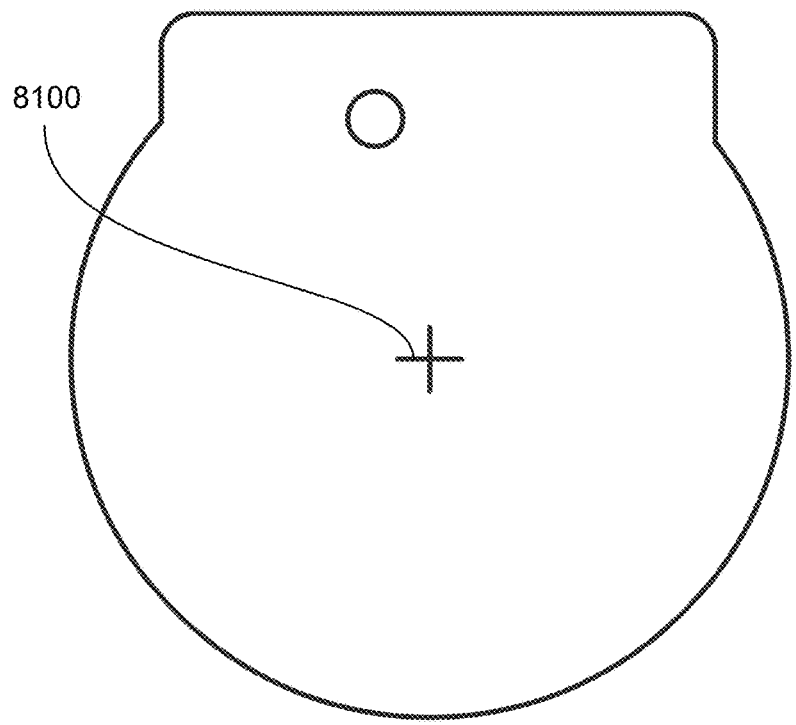
FIG. 8 is a block diagram of an exemplary embodiment of a system 8000.

FIG. 8 is a block diagram of an exemplary embodiment of a system 8000, which illustrates a split center pin 8100, which can be keyed. Split center pin 8100 rotates to load a blister strip. FIG. 8 is a rear view of a case, which is substantially opposite a hinged cover.

Figure 9:
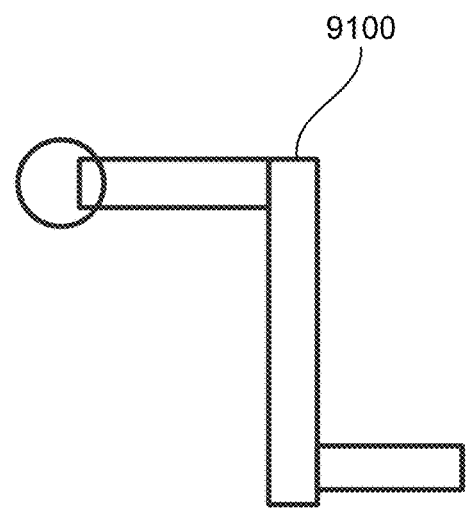
FIG. 9 is a block diagram of an exemplary embodiment of a square keyed load tool 9000.

FIG. 9 is a block diagram of an exemplary embodiment of a square keyed load tool 9000.

Figure 10:
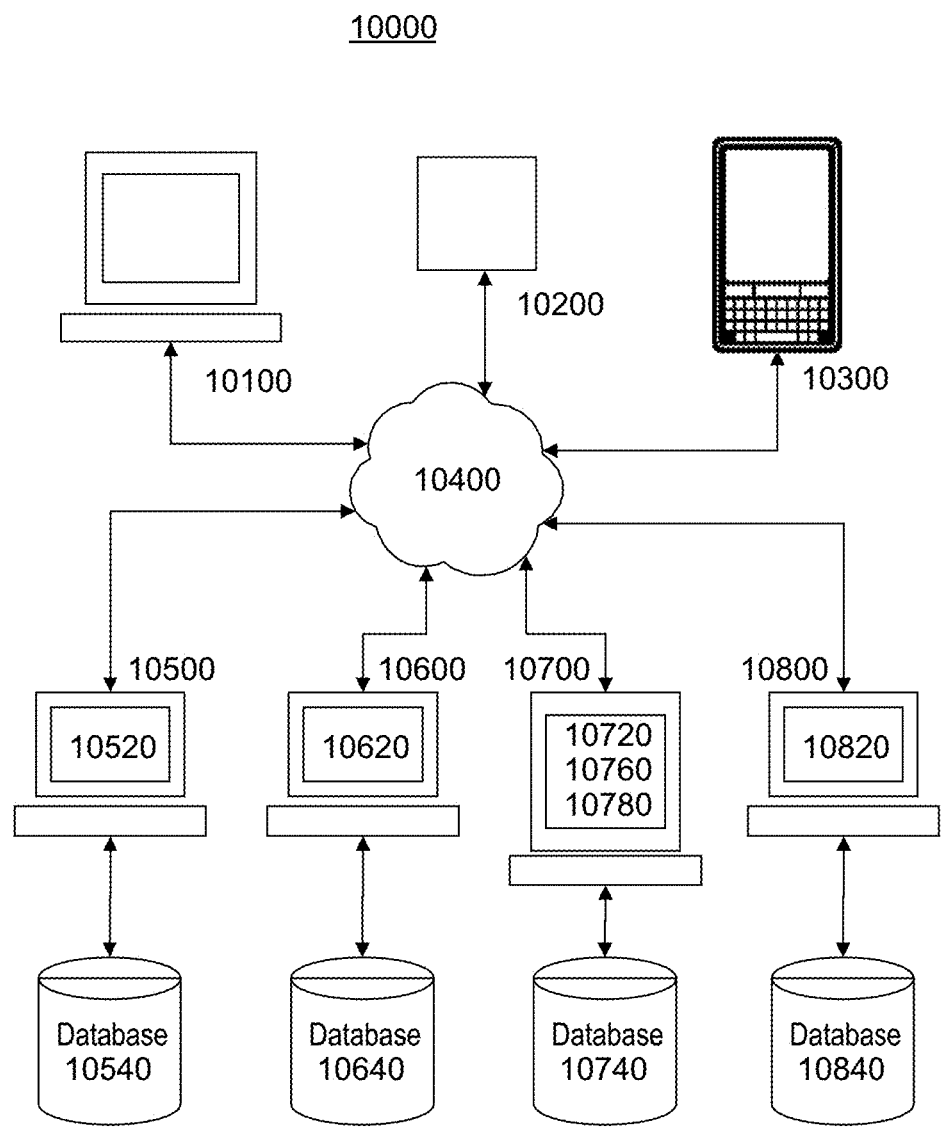
FIG. 10 is a block diagram of an exemplary embodiment of a system 10000.

FIG. 10 is a block diagram of an exemplary embodiment of a system 10000, which can comprise a smartphone 10300, an information device 10100, tablet 10200, a network 10400, a first server 10500, a second server 10600, a third server 10700, and a fourth server 10800. First server 10500 can comprise a first user interface 10520 and can be coupled to a first database 10540. Second server 10600 can comprise a second user interface 10620 and can be coupled to a second database 10640. Third server 10700 can comprise a third user interface 10720, a processor 10760, machine instructions 10780, and can be coupled to a third database 10740. Fourth server 10800 can comprise a fourth user interface 10820 and can be coupled to a fourth database 10840. Any of the methods and/or steps thereof can be carried out in whole or in part by tablet 10200, smartphone 10300, information device 10100 and/or first server 10500. Second server 10600, third server 10700, and/or fourth server 10800 can each be associated with implementation of a system via which medicaments can be dispersed via a blister strip dispenser. In certain exemplary embodiments, system 10000 can be used to implement one or more methods disclosed herein.

Figure 11:
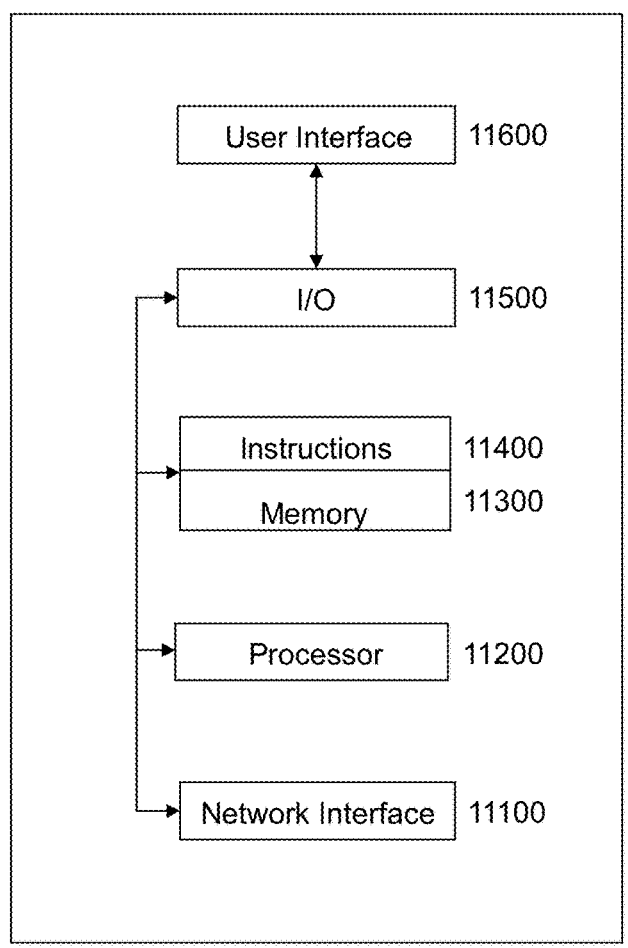
FIG. 11 is a block diagram of an exemplary embodiment of an information device 1000.

FIG. 11 is a block diagram of an exemplary embodiment of an information device 11000, which in certain operative embodiments can comprise, for example, information device 10100 of FIG. 10. Information device 11000 can comprise any of numerous circuits and/or components, such as for example, one or more network interfaces 11100, one or more processors 11200, one or more memories 11300 ing instructions 11400, one or more input/output (I/O) devices 11500, and/or one or more user interfaces 11600 coupled to I/O device 11500, etc.

In certain exemplary embodiments, via one or more user interfaces 11600, such as a graphical user interface, a user can view a rendering of information related to researching, designing, modeling, creating, developing, building, manufacturing, operating, maintaining, storing, marketing, selling, delivering, selecting, specifying, requesting, ordering, receiving, returning, rating, and/or recommending any of the products, services, methods, and/or information described herein.

DEFINITIONS

When the following terms are used substantively herein, the accompanying definitions apply. These terms and definitions are presented without prejudice, and, consistent with the application, the right to redefine these terms during the prosecution of this application or any application claiming priority hereto is reserved. For the purpose of interpreting a claim of any patent that claims priority hereto, each definition (or redefined term if an original definition was amended during the prosecution of that patent), functions as a clear and unambiguous disavowal of the subject matter outside of that definition.

a—at least one.
action—something done.
activity—an action, act, step, and/or process or portion thereof.
adapter—a device used to effect operative compatibility between different parts of one or more pieces of an apparatus or system.
advance—to move to a more forward position.
align—to guide to a desired location along a line.
allow—to position so as to facilitate an action.
and/or—either in conjunction with or in alternative to.
apparatus—an appliance or device for a particular purpose.
approach—to move nearer to.
associate—to join, connect together, and/or relate.
audible sound—a noise detectable to a human's ear.
authorized—permitted by an authority.
automatically—acting or operating in a manner essentially independent of external influence or control. For example, an automatic light switch can turn on upon "seeing" a person in its view, without the person manually operating the light switch.
backing—a rear surface lining of a blister strip (e.g., a foil lining).
biometric identification—determining who a person is via one or more measured metrics of human physiology (e.g., fingerprint, palm veins, face recognition, DNA, palm print, hand geometry, iris recognition, retina, and/or scent, etc.).
blister strip—a sheet of plastic with pockets that comprise pills, tablets, and/or capsules. Blister strip can be sealed with a thin sheet of aluminum foil.
body—a largest or principal part of a case.
can—is capable of, in at least some embodiments.
case—a container constructed to house a blister strip.
cause—to produce an effect.
chamber—a compartment or cavity.
childproof button—a lock constructed to resist easy access to a case by a youth.
closeable—constructed to obstruct access to a cavity.
close communication—in proximity to such that surfaces are either touching or within a millimeter of touching.
circuit—an electrically conductive pathway and/or a communications connection established across two or more switching devices comprised by a network and between corresponding end systems connected to, but not comprised by the network.
comprising—including but not limited to.
configure—to make suitable or fit for a specific use or situation.
connect—to join or fasten together.
constructed to—made to and/or designed to.
contact—to touch.
controller—a device and/or set of machine-readable instructions for performing one or more predetermined tasks. A controller can comprise any one or a combination of hardware, firmware, and/or software. A controller can utilize mechanical, pneumatic, hydraulic, electrical, magnetic, optical, informational, chemical, and/or biological principles, signals, and/or inputs to perform the task(s). In certain embodiments, a controller can act upon information by manipulating, analyzing, modifying, converting, transmitting the information for use by an executable procedure and/or an information device, and/or routing the information to an output device. A controller can be a central processing unit, a local controller, a remote controller, parallel controllers, and/or distributed controllers, etc. The controller can be a general-purpose microcontroller, such the Pentium IV series of microprocessor manufactured by the Intel Corporation of Santa Clara, Calif. In another embodiment, the controller can be an Application Specific Integrated Circuit (ASIC) or a Field Programmable Gate Array (FPGA) that has been designed to implement in its hardware and/or firmware at least a part of an embodiment disclosed herein.
convert—to transform, adapt, and/or change.
couple—to link in some fashion.
coupleable—capable of being joined, connected, and/or linked together.
cover—a component constructed to lie on or over a cavity in order to control ingress and/or egress via the cavity.
create—to bring into being.

data—distinct pieces of information, usually formatted in a special or predetermined way and/or organized to express concepts.
define—to establish the outline, form, or structure of.
determine—to obtain, calculate, decide, deduce, and/or ascertain.
device—a machine, manufacture, and/or collection thereof.
dispense—to give out or issue in portions.
engage—to be in contact and interact with.
entry—a way into a space.
exit—a way out of a space.
fingerprint sensor—a detector that measures characteristics of a surface of an end of a human digit.
fixed—fastened, attached, and/or placed so as to be firm and not readily movable relative to another component.
generate—to cause creation of.
guide—a component constructed to directing motion of a blister strip.
hold—to contain something.
haptic—involving the human sense of kinesthetic movement and/or the human sense of touch. Among the many potential haptic experiences are numerous sensations, body-positional differences in sensations, and time-based changes in sensations that are perceived at least partially in non-visual, non-audible, and non-olfactory manners, including the experiences of tactile touch (being touched), active touch, grasping, pressure, friction, traction, slip, stretch, force, torque, impact, puncture, vibration, motion, acceleration, jerk, pulse, orientation, limb position, gravity, texture, gap, recess, viscosity, pain, itch, moisture, temperature, thermal conductivity, and thermal capacity.
hinge—a mechanical bearing that connects two components, which allows rotation between the two components.
information device—any device capable of processing data and/or information, such as any general purpose and/or special purpose computer, such as a personal computer, workstation, server, minicomputer, mainframe, supercomputer, computer terminal, laptop, wearable computer, and/or Personal Digital Assistant (PDA), mobile terminal, Bluetooth device, communicator, "smart" phone (such as a Treo-like device), messaging service (e.g., Blackberry) receiver, pager, facsimile, cellular telephone, a traditional telephone, telephonic device, a programmed microprocessor or microcontroller and/or peripheral integrated circuit elements, an ASIC or other integrated circuit, a hardware electronic logic circuit such as a discrete element circuit, and/or a programmable logic device such as a PLD, PLA, FPGA, or PAL, or the like, etc. In general any device on which resides a finite state machine capable of implementing at least a portion of a method, structure, and/or or graphical user interface described herein may be used as an information device. An information device can comprise components such as one or more network interfaces, one or more processors, one or more memories containing instructions, and/or one or more input/output (I/O) devices, one or more user interfaces coupled to an I/O device, etc.
initialize—to prepare something for use and/or some future event.
input/output (I/O) device—any sensory-oriented input and/or output device, such as an audio, visual, haptic, olfactory, and/or taste-oriented device, including, for example, a monitor, display, projector, overhead display, keyboard, keypad, mouse, trackball, joystick, gamepad, wheel, touchpad, touch panel, pointing device, microphone, speaker, video camera, camera, scanner, printer, haptic device, vibrator, tactile simulator, and/or tactile pad, potentially including a port to which an I/O device can be attached or connected.
install—to connect or set in position and prepare for use.
keyed—an implement constructed to engage with something that can be turned to accomplish an objective.
latch—a mechanical fastener that joins two surfaces while allowing for their releasable separation.
light—a source of illumination.
light emitting diode—a two-lead semiconductor light source, which is a p-n junction diode that emits light when activated.
lever—a device comprising a rod pivoted at a fixed hinge.
lift—to move something to a higher position relative to something else.
linear thumb slide—a moveable control operable by a human digit.
load—to place a blister strip in a case in a predetermined manner.
lock—to secure so as to resist access by a human.
machine instructions—directions adapted to cause a machine, such as an information device, to perform one or more particular activities, operations, or functions. The directions, which can sometimes form an entity called a "processor", "kernel", "operating system", "program", "application", "utility", "subroutine", "script", "macro", "file", "project", "module", "library", "class", and/or "object", etc., can be embodied as machine code, source code, object code, compiled code, assembled code, interpretable code, and/or executable code, etc., in hardware, firmware, and/or software.
machine readable medium—a physical structure from which a machine can obtain data and/or information. Examples include a memory, punch cards, etc.
may—is allowed and/or permitted to, in at least some embodiments.
memory device—an apparatus capable of storing analog or digital information, such as instructions and/or data. Examples include a non-volatile memory, volatile memory, Random Access Memory, RAM, Read Only Memory, ROM, flash memory, magnetic media, a hard disk, a floppy disk, a magnetic tape, an optical media, an optical disk, a compact disk, a CD, a digital versatile disk, a DVD, and/or a raid array, etc. The memory device can be coupled to a processor and/or can store instructions adapted to be executed by processor, such as according to an embodiment disclosed herein.
method—a process, procedure, and/or collection of related activities for accomplishing something.
movement—a change from a first position to a second position.
network—a communicatively coupled plurality of nodes. A network can be and/or utilize any of a wide variety of sub-networks, such as a circuit switched, public-switched, packet switched, data, telephone, telecommunications, video distribution, cable, terrestrial, broadcast, satellite, broadband, corporate, global, national, regional, wide area, backbone, packet-switched TCP/IP, Fast Ethernet, Token Ring, public Internet, private, ATM, multi-domain, and/or multi-zone sub-network, one or more Internet service providers, and/or one or more information devices, such as a switch, router, and/or gateway not directly connected to a local area network, etc.

network interface—any device, system, or subsystem capable of coupling an information device to a network. For example, a network interface can be a telephone, cellular phone, cellular modem, telephone data modem, fax modem, wireless transceiver, ethernet card, cable modem, digital subscriber line interface, bridge, hub, router, or other similar device.

packet—a discrete instance of communication.

partial—not in total.

pass—to convey to a desired location.

passage—a corridor or pathway through something.

pill—a tablet or capsule, such as of medicine.

pin—a slender piece of solid material.

pivot—a component that comprises a point of rotation in a lever system.

plurality—the state of being plural and/or more than one.

port—an opening constructed to pass a pill and/or tablet in a blister strip.

portion—a part of a whole.

position—location.

predetermined—established in advance.

prescription—an order for medicine.

processor—a device and/or set of machine-readable instructions for performing one or more predetermined tasks. A processor can comprise any one or a combination of hardware, firmware, and/or software. A processor can utilize mechanical, pneumatic, hydraulic, electrical, magnetic, optical, informational, chemical, and/or biological principles, signals, and/or inputs to perform the task(s). In certain embodiments, a processor can act upon information by manipulating, analyzing, modifying, converting, transmitting the information for use by an executable procedure and/or an information device, and/or routing the information to an output device. A processor can function as a central processing unit, local controller, remote controller, parallel controller, and/or distributed controller, etc. Unless stated otherwise, the processor can be a general-purpose device, such as a microcontroller and/or a microprocessor, such the Pentium IV series of microprocessor manufactured by the Intel Corporation of Santa Clara, Calif. In certain embodiments, the processor can be dedicated purpose device, such as an Application Specific Integrated Circuit (ASIC) or a Field Programmable Gate Array (FPGA) that has been designed to implement in its hardware and/or firmware at least a part of an embodiment disclosed herein.

project—to calculate, estimate, or predict.

provide—to furnish, supply, give, and/or make available.

receive—to get as a signal, take, acquire, and/or obtain.

receptacle—a port defined by an object, which port is constructed to receive a latch and thereby hold components together relative to each other.

record—to store a historical accounting.

related to—connected to and/or associated with.

releasably—coupled so as to be substantially nondestructibly removable.

release—to free from something that binds, fastens, or holds back; to let go.

render—to make perceptible to a human, for example as data, commands, text, graphics, audio, video, animation, and/or hyperlinks, etc., such as via any visual, audio, and/or haptic means, such as via a display, monitor, electric paper, ocular implant, cochlear implant, speaker, etc.

repeatedly—again and again; repetitively.

request—to express a desire for and/or ask for.

resist—to oppose something.

responsive—reacting to an influence and/or impetus.

select—to make a choice or selection from alternatives.

sensor—a device used to measure a physical quantity (e.g., temperature, pressure, capacitance, and/or loudness, etc.) and convert that physical quantity into a signal of some kind (e.g., voltage, current, power, etc.). A sensor can be any instrument such as, for example, any instrument measuring pressure, temperature, flow, mass, heat, light, sound, humidity, proximity, position, velocity, vibration, voltage, current, capacitance, resistance, inductance, and/or electro-magnetic radiation, etc. Such instruments can comprise, for example, proximity switches, photo sensors, thermocouples, level indicating devices, speed sensors, electrical voltage indicators, electrical current indicators, on/off indicators, and/or flowmeters, etc.

set—a related plurality.

signal—information, such as machine instructions for activities and/or one or more letters, words, characters, symbols, signal flags, visual displays, and/or special sounds, etc. having prearranged meaning, encoded as automatically detectable variations in a physical variable, such as a pneumatic, hydraulic, acoustic, fluidic, mechanical, electrical, magnetic, optical, chemical, and/or biological variable, such as power, energy, pressure, flowrate, viscosity, density, torque, impact, force, frequency, phase, voltage, current, resistance, magnetomotive force, magnetic field intensity, magnetic field flux, magnetic flux density, reluctance, permeability, index of refraction, optical wavelength, polarization, reflectance, transmittance, phase shift, concentration, and/or temperature, etc. Depending on the context, a signal and/or the information encoded therein can be synchronous, asynchronous, hard real-time, soft real-time, non-real time, continuously generated, continuously varying, analog, discretely generated, discretely varying, quantized, digital, broadcast, multicast, unicast, transmitted, conveyed, received, continuously measured, discretely measured, processed, encoded, encrypted, multiplexed, modulated, spread, de-spread, demodulated, detected, de-multiplexed, decrypted, and/or decoded, etc.

size—to have a sufficient diameter to pass a pill having a predetermined diameter.

split center—defining a slot substantially along a middle axis.

store—to place, hold, and/or retain.

substantially—to a great extent or degree.

support—to bear the weight of, especially from below.

system—a collection of mechanisms, devices, machines, articles of manufacture, processes, data, and/or instructions, the collection designed to perform one or more specific functions.

tablet—a small mass of medicated material.

tamper—to meddle for the purpose of altering, damaging, or misusing.

tear—to pull and thereby rend from something.

timing—a determination of when something happens.

tool—implement.

transducer—a device that converts one form of energy into another. For example, a sensing optical fiber can convert changes in mechanical energy, such as a perturbation of the fiber, to changes in optical energy.

transmit—to send as a signal, provide, furnish, and/or supply.

user interface—any device for rendering information to a user and/or requesting information from the user. A user interface includes at least one of textual, graphical, audio, video, animation, and/or haptic elements. A textual element can be provided, for example, by a printer, monitor, display, projector, etc. A graphical element can be provided, for example, via a monitor, display, projector, and/or visual indication device, such as a light, flag, beacon, etc. An audio element can be provided, for example, via a speaker, microphone, and/or other sound generating and/or receiving device. A video element or animation element can be provided, for example, via a monitor, display, projector, and/or other visual device. A haptic element can be provided, for example, via a very low frequency speaker, vibrator, tactile stimulator, tactile pad, simulator, keyboard, keypad, mouse, trackball, joystick, gamepad, wheel, touchpad, touch panel, pointing device, and/or other haptic device, etc. A user interface can include one or more textual elements such as, for example, one or more letters, number, symbols, etc. A user interface can include one or more graphical elements such as, for example, an image, photograph, drawing, icon, window, title bar, panel, sheet, tab, drawer, matrix, table, form, calendar, outline view, frame, dialog box, static text, text box, list, pick list, pop-up list, pull-down list, menu, tool bar, dock, check box, radio button, hyperlink, browser, button, control, palette, preview panel, color wheel, dial, slider, scroll bar, cursor, status bar, stepper, and/or progress indicator, etc. A textual and/or graphical element can be used for selecting, programming, adjusting, changing, specifying, etc. an appearance, background color, background style, border style, border thickness, foreground color, font, font style, font size, alignment, line spacing, indent, maximum data length, validation, query, cursor type, pointer type, autosizing, position, and/or dimension, etc. A user interface can include one or more audio elements such as, for example, a volume control, pitch control, speed control, voice selector, and/or one or more elements for controlling audio play, speed, pause, fast forward, reverse, etc. A user interface can include one or more video elements such as, for example, elements controlling video play, speed, pause, fast forward, reverse, zoom-in, zoom-out, rotate, and/or tilt, etc. A user interface can include one or more animation elements such as, for example, elements controlling animation play, pause, fast forward, reverse, zoom-in, zoom-out, rotate, tilt, color, intensity, speed, frequency, appearance, etc. A user interface can include one or more haptic elements such as, for example, elements utilizing tactile stimulus, force, pressure, vibration, motion, displacement, temperature, etc.

via—by way of and/or utilizing.

visible illumination—light energy detected by a human eye.

waterproof—substantially impervious to penetration by a liquid.

weight—a value indicative of importance.

Note

Still other substantially and specifically practical and useful embodiments will become readily apparent to those skilled in this art from reading the above-recited and/or herein-included detailed description and/or drawings of certain exemplary embodiments. It should be understood that numerous variations, modifications, and additional embodiments are possible, and accordingly, all such variations, modifications, and embodiments are to be regarded as being within the scope of this application.

Thus, regardless of the content of any portion (e.g., title, field, background, summary, description, abstract, drawing figure, etc.) of this application, unless clearly specified to the contrary, such as via explicit definition, assertion, or argument, with respect to any claim, whether of this application and/or any claim of any application claiming priority hereto, and whether originally presented or otherwise:

there is no requirement for the inclusion of any particular described or illustrated characteristic, function, activity, or element, any particular sequence of activities, or any particular interrelationship of elements;

no characteristic, function, activity, or element is "essential";

any elements can be integrated, segregated, and/or duplicated;

any activity can be repeated, any activity can be performed by multiple entities, and/or any activity can be performed in multiple jurisdictions; and any activity or element can be specifically excluded, the sequence of activities can vary, and/or the interrelationship of elements can vary.

Moreover, when any number or range is described herein, unless clearly stated otherwise, that number or range is approximate. When any range is described herein, unless clearly stated otherwise, that range includes all values therein and all subranges therein. For example, if a range of 1 to 10 is described, that range includes all values therebetween, such as for example, 1.1, 2.5, 3.335, 5, 6.179, 8.9999, etc., and includes all subranges therebetween, such as for example, 1 to 3.65, 2.8 to 8.14, 1.93 to 9, etc.

When any claim element is followed by a drawing element number, that drawing element number is exemplary and non-limiting on claim scope. No claim of this application is intended to invoke paragraph six of 35 USC 112 unless the precise phrase "means for" is followed by a gerund.

Any information in any material (e.g., a United States patent, United States patent application, book, article, etc.) that has been incorporated by reference herein, is only incorporated by reference to the extent that no conflict exists between such information and the other statements and drawings set forth herein. In the event of such conflict, including a conflict that would render invalid any claim herein or seeking priority hereto, then any such conflicting information in such material is specifically not incorporated by reference herein.

Accordingly, every portion (e.g., title, field, background, summary, description, abstract, drawing figure, etc.) of this application, other than the claims themselves, is to be regarded as illustrative in nature, and not as restrictive, and the scope of subject matter protected by any patent that issues based on this application is defined only by the claims of that patent.

What is claimed is:

1. A system comprising:
    a case comprising:
        a body comprising a lever, the body defining a cover latch aperture and a dispensing port;
        a cover coupled to the body via a hinge, wherein the cover is releasably closeable with the body via a cover latch and the cover latch aperture;
        a keyed, split center pin that is constructed to engage with a first end of a blister strip;

a first guide that aligns the blister strip with the dispensing port, wherein the first guide is at least in partial contact with blister strip backing; and a first dispense latch constructed to lift as a tablet comprised by the blister strip passes to the dispensing port;

a dispense latch lock that engages with the first dispense latch; and allows a tearing of the blister strip substantially without advancing the blister strip in the case; and wherein the case is constructed to release a tablet from the blister strip responsive to movement of the lever.

2. The system of claim 1, wherein:
the case is substantially waterproof.

3. The system of claim 1, wherein:
the lever is a linear thumb slide.

4. The system of claim 1, further comprising:
an information device coupled to the case, wherein the information device is constructed to control dispensing of tablets from the blister strip responsive to a biometric identification of a user.

5. The system of claim 1, further comprising:
a fingerprint sensor constructed to transmit a signal indicative of a fingerprint of an authorized user such that a tablet is dispensed from the case.

6. The system of claim 1, further comprising:
a tamper detection sensor constructed to indicate when the cover is opened.

7. The system of claim 1, further comprising:
a load tool constructed to engage with the split center pin, wherein a user loads the blister strip in the case via rotation of the load tool.

8. The system of claim 1, further comprising:
a childproof button constructed to, when in a locked position, resist dispensing of a tablet.

9. The system of claim 1, further comprising:
a sound transducer that generates an audible sound in response to an action of a user related to dispensing a tablet from the blister strip.

10. The system of claim 1, further comprising:
a light that generates a visible illumination in response to an action of a user related to dispensing a tablet from the blister strip.

11. The system of claim 1, further comprising:
a second guide that resists motion of the blister strip away from the first guide as a tablet of the blister strip approaches the dispensing port.

* * * * *